United States Patent
Oron et al.

(10) Patent No.: US 10,369,366 B2
(45) Date of Patent: Aug. 6, 2019

(54) IMPLANTABLE ELECTROSTIMULATOR FOR IMPROVING BLOOD FLOW

(71) Applicant: BLUEWIND MEDICAL LTD., Herzlia (IL)

(72) Inventors: Gur Oron, Tel Aviv (IL); Yossi Gross, Moshav Mazor (IL); Bar Eytan, Gedera (IL); Eran Benjamin, Tel-Aviv (IL); Karin Aharonson-Raz, Karmey Yosef (IL)

(73) Assignee: BLUEWIND MEDICAL LTD., Herzliya (IL)

( * ) Notice: Subject to any disclaimer, the term of this patent is extended or adjusted under 35 U.S.C. 154(b) by 0 days.

(21) Appl. No.: 15/726,971

(22) Filed: Oct. 6, 2017

(65) Prior Publication Data
US 2018/0028816 A1 Feb. 1, 2018

Related U.S. Application Data

(63) Continuation of application No. 14/735,741, filed on Jun. 10, 2015, now Pat. No. 9,782,589.

(51) Int. Cl.
*A61N 1/36* (2006.01)
*A61N 1/375* (2006.01)
(Continued)

(52) U.S. Cl.
CPC ........ *A61N 1/36135* (2013.01); *A61N 1/3606* (2013.01); *A61N 1/3756* (2013.01); *A61N 1/37205* (2013.01); *A61N 1/3787* (2013.01)

(58) Field of Classification Search
CPC .............. A61N 1/36135; A61N 1/3606; A61N 1/36067; A61N 1/3756; A61N 1/3787;
(Continued)

(56) References Cited

U.S. PATENT DOCUMENTS 3,411,507 A 11/1968 Wingrove
3,693,625 A 9/1972 Auphan
(Continued)

FOREIGN PATENT DOCUMENTS

DE 102008054403 6/2010
EP 0 688 577 12/1995
(Continued)

OTHER PUBLICATIONS

C. de Balthasar, G. Cosendai, M. Hansen, D. Canfield, L. Chu, R. Davis, and J. Schulman, "Attachment of leads to RF-BION® microstimulators." Jul. 2005.
(Continued)

*Primary Examiner* — Tammie K Marlen
(74) *Attorney, Agent, or Firm* — Sughrue Mion, PLLC (57) ABSTRACT

Apparatus includes an implant and an introducer. The implant includes an injectable housing, an electrode disposed on an outer surface of the housing, and circuitry. The circuitry is configured to alternate between a first mode in which the circuitry drives the electrode to apply a first electrical current having a frequency of 1-100 Hz, and a second mode in which the implant applies a second electrical current having a frequency of 1-10 kHz. The introducer includes a tube that defines a lumen and is percutaneously-advanceable into tissue of the subject, the lumen being dimensioned to at least temporarily house the implant. The introducer is configured to deploy the implant from a distal end of the lumen by moving the implant and the distal end of the lumen relative to each other. Other embodiments are also described.

13 Claims, 5 Drawing Sheets

(51) Int. Cl.
*A61N 1/372* (2006.01)
*A61N 1/378* (2006.01)

(58) Field of Classification Search
CPC .......... A61N 1/36003; A61N 1/36014; A61N 1/37205; A61N 1/36017
See application file for complete search history.

(56) References Cited

U.S. PATENT DOCUMENTS

| | | |
|---|---|---|
| 3,727,616 A | 4/1973 | Lenzkes |
| 4,019,518 A | 4/1977 | Maurer et al. |
| 4,338,945 A | 7/1982 | Kosugi et al. |
| 4,392,496 A | 7/1983 | Stanton |
| 4,535,785 A | 8/1985 | Van Den Honert |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples |
| 4,608,985 A | 9/1986 | Crish |
| 4,628,942 A | 12/1986 | Sweeney |
| 4,632,116 A | 12/1986 | Rosen |
| 4,649,936 A | 3/1987 | Ungar |
| 4,663,102 A | 5/1987 | Brenman et al. |
| 4,739,764 A | 4/1988 | Lau |
| 4,808,157 A | 2/1989 | Coombs |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,036,854 A | 8/1991 | Schollmeyer et al. |
| 5,069,680 A | 12/1991 | Grandjean |
| 5,178,161 A | 1/1993 | Kovacs |
| 5,188,104 A | 2/1993 | Wernicke |
| 5,199,428 A | 4/1993 | Obel et al. |
| 5,199,430 A | 4/1993 | Fang |
| 5,203,326 A | 4/1993 | Collins |
| 5,205,285 A | 4/1993 | Baker, Jr. |
| 5,215,086 A | 6/1993 | Terry, Jr. |
| 5,263,480 A | 11/1993 | Wernicke |
| 5,282,468 A | 2/1994 | Klepinski |
| 5,284,479 A | 2/1994 | De Jong |
| 5,292,344 A | 3/1994 | Douglas |
| 5,299,569 A | 4/1994 | Wernicke |
| 5,314,495 A | 5/1994 | Kovacs |
| 5,330,507 A | 7/1994 | Schwartz |
| 5,335,657 A | 8/1994 | Terry, Jr. |
| 5,411,535 A | 5/1995 | Fujii et al. |
| 5,423,872 A | 6/1995 | Cigaina |
| 5,439,938 A | 8/1995 | Synder et al. |
| 5,454,840 A | 10/1995 | Krakovsky et al. |
| 5,487,760 A | 1/1996 | Villafana |
| 5,505,201 A | 4/1996 | Grill, Jr. |
| 5,540,730 A | 7/1996 | Terry, Jr. |
| 5,540,733 A | 7/1996 | Testerman et al. |
| 5,540,734 A | 7/1996 | Zabara |
| 5,549,655 A | 8/1996 | Erickson |
| 5,571,150 A | 11/1996 | Wernicke |
| 5,591,216 A | 1/1997 | Testerman et al. |
| 5,634,462 A | 6/1997 | Tyler et al. |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry, Jr. |
| 5,711,316 A | 1/1998 | Elsberry et al. |
| 5,716,385 A | 2/1998 | Mittal |
| 5,755,750 A | 5/1998 | Petruska |
| 5,776,170 A | 7/1998 | Macdonald et al. |
| 5,776,171 A | 7/1998 | Peckham |
| 5,814,089 A | 9/1998 | Stokes |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,916,239 A | 6/1999 | Geddes et al. |
| 5,938,584 A | 8/1999 | Ardito et al. |
| 5,944,680 A | 8/1999 | Christopherson |
| 5,954,758 A | 9/1999 | Peckham |
| 5,991,664 A | 11/1999 | Seligman |
| 6,002,964 A | 12/1999 | Feler et al. |
| 6,026,326 A | 2/2000 | Bardy |
| 6,026,328 A | 2/2000 | Peckham |
| 6,032,076 A | 2/2000 | Melvin et al. |
| 6,058,331 A | 5/2000 | King et al. |
| 6,066,163 A | 5/2000 | John |
| 6,071,274 A | 6/2000 | Thompson et al. |
| 6,091,992 A | 6/2000 | Bourgeois |
| 6,083,249 A | 7/2000 | Familoni |
| 6,086,525 A | 7/2000 | Davey et al. |
| 6,091,977 A | 7/2000 | Tarjan et al. |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| 6,146,335 A | 11/2000 | Gozani |
| 6,148,232 A | 11/2000 | Avrahami |
| 6,161,048 A | 12/2000 | Sluijter et al. |
| 6,169,924 B1 | 1/2001 | Meloy et al. |
| 6,205,359 B1 | 3/2001 | Boveja |
| 6,212,435 B1 | 4/2001 | Lattner et al. |
| 6,214,032 B1 | 4/2001 | Loeb et al. |
| 6,230,061 B1 | 5/2001 | Hartung |
| 6,240,316 B1 | 5/2001 | Richmond |
| 6,246,912 B1 | 6/2001 | Sluijter et al. |
| 6,266,564 B1 | 7/2001 | Schwartz |
| 6,272,383 B1 | 8/2001 | Grey |
| 6,292,703 B1 | 9/2001 | Meier et al. |
| 6,319,241 B1 | 11/2001 | King |
| 6,332,089 B1 | 12/2001 | Acker |
| 6,341,236 B1 | 1/2002 | Osorio et al. |
| 6,345,202 B2 | 2/2002 | Richmond et al. |
| 6,356,784 B1 | 3/2002 | Lozano et al. |
| 6,356,788 B2 | 3/2002 | Boveja |
| 6,366,813 B1 | 4/2002 | Dilorenzo |
| 6,405,079 B1 | 6/2002 | Ansarinia |
| 6,442,432 B2 | 8/2002 | Lee |
| 6,445,953 B1 | 9/2002 | Bulkes et al. |
| 6,449,507 B1 | 9/2002 | Hill et al. |
| 6,456,878 B1 | 9/2002 | Yerich et al. |
| 6,463,328 B1 | 10/2002 | John |
| 6,473,644 B1 | 10/2002 | Terry, Jr. et al. |
| 6,496,729 B2 | 12/2002 | Thompson |
| 6,496,730 B1 | 12/2002 | Kleckner et al. |
| 6,600,954 B2 | 7/2003 | Cohen |
| 6,600,956 B2 | 7/2003 | Maschino et al. |
| 6,606,521 B2 | 8/2003 | Paspa et al. |
| 6,610,713 B2 | 8/2003 | Tracey |
| 6,618,627 B2 | 9/2003 | Lattner et al. |
| 6,641,542 B2 | 11/2003 | Cho et al. |
| 6,735,474 B1 | 5/2004 | Loeb et al. |
| 6,770,022 B2 | 8/2004 | Mechlenburg |
| 6,829,508 B2 | 12/2004 | Schulman |
| 6,839,594 B2 | 1/2005 | Cohen |
| 6,892,098 B2 | 5/2005 | Ayal |
| 6,909,917 B2 | 6/2005 | Woods et al. |
| 7,025,730 B2 | 4/2006 | Cho et al. |
| 7,027,860 B2 | 4/2006 | Bruninga et al. |
| 7,047,076 B1 | 5/2006 | Li et al. |
| 7,054,692 B1 | 5/2006 | Whitehurst et al. |
| 7,149,575 B2 | 12/2006 | Ostroff et al. |
| 7,177,698 B2 | 2/2007 | Klosterman et al. |
| 7,212,867 B2 | 5/2007 | Venrooij et al. |
| 7,228,178 B2 | 6/2007 | Carroll |
| 7,277,749 B2 | 10/2007 | Gordon et al. |
| 7,289,853 B1 | 10/2007 | Campbell et al. |
| 7,324,852 B2 | 1/2008 | Barolat et al. |
| 7,324,853 B2 | 1/2008 | Ayal |
| 7,389,145 B2 | 6/2008 | Kilgore et al. |
| 7,483,752 B2 | 1/2009 | Von arx et al. |
| 7,532,932 B2 | 5/2009 | Denker et al. |
| 7,536,226 B2 | 5/2009 | Williams |
| 7,628,750 B2 | 12/2009 | Cohen |
| 7,630,771 B2 | 12/2009 | Cauller |
| 7,634,313 B1 | 12/2009 | Kroll et al. |

(56) References Cited

U.S. PATENT DOCUMENTS

| | | |
|---|---|---|
| 7,655,014 B2 | 2/2010 | Ko et al. |
| 7,657,311 B2 | 2/2010 | Bardy et al. |
| 7,657,322 B2 | 2/2010 | Bardy et al. |
| 7,660,632 B2 | 2/2010 | Kirby et al. |
| 7,680,538 B2 | 3/2010 | Durand et al. |
| 7,711,434 B2 | 5/2010 | Denker et al. |
| 7,736,379 B2 | 6/2010 | Ewers et al. |
| 7,780,625 B2 | 8/2010 | Bardy |
| 7,797,050 B2 | 9/2010 | Libbus et al. |
| 7,803,142 B2 | 9/2010 | Longson et al. |
| 7,848,818 B2 | 12/2010 | Barolat et al. |
| 7,917,226 B2 | 5/2011 | Nghiem |
| 7,937,148 B2 | 5/2011 | Jacobson |
| 7,941,218 B2 | 5/2011 | Sambelashvili et al. |
| 7,974,706 B2 | 7/2011 | Moffitt et al. |
| 7,991,467 B2 | 8/2011 | Markowitz et al. |
| 7,996,089 B2 | 8/2011 | Haugland et al. |
| 7,996,092 B2 | 8/2011 | Mrva et al. |
| 8,019,443 B2 | 9/2011 | Scheicher et al. |
| 8,055,350 B2 | 11/2011 | Roberts |
| 8,075,556 B2 | 12/2011 | Betts |
| 8,090,438 B2 | 1/2012 | Bardy et al. |
| 8,131,377 B2 | 3/2012 | Shhi et al. |
| 8,170,675 B2 | 5/2012 | Alataris et al. |
| 8,177,792 B2 | 5/2012 | Lubock et al. |
| 8,185,207 B2 | 5/2012 | Molnar et al. |
| 8,209,021 B2 | 6/2012 | Alataris et al. |
| 8,224,453 B2 | 7/2012 | De Ridder |
| 8,255,057 B2 | 8/2012 | Fang et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,396,559 B2 | 3/2013 | Alataris et al. |
| 8,428,748 B2 | 4/2013 | Alataris et al. |
| 8,509,905 B2 | 8/2013 | Alataris et al. |
| 8,509,906 B2 | 8/2013 | Walker et al. |
| 8,554,326 B2 | 10/2013 | Alataris et al. |
| 8,634,927 B2 | 1/2014 | Olson et al. |
| 8,649,874 B2 | 2/2014 | Alataris et al. |
| 8,694,108 B2 | 4/2014 | Alataris et al. |
| 8,694,109 B2 | 4/2014 | Alataris et al. |
| 8,712,533 B2 | 4/2014 | Alataris et al. |
| 8,718,781 B2 | 5/2014 | Alataris et al. |
| 8,718,782 B2 | 5/2014 | Alataris et al. |
| 8,755,893 B2 | 6/2014 | Gross et al. |
| 8,768,472 B2 | 7/2014 | Fang et al. |
| 8,774,926 B2 | 7/2014 | Alataris et al. |
| 8,788,045 B2 | 7/2014 | Gross et al. |
| 8,792,988 B2 | 7/2014 | Alataris et al. |
| 8,849,410 B2 | 9/2014 | Walker et al. |
| 8,862,239 B2 | 10/2014 | Alataris et al. |
| 8,868,192 B2 | 10/2014 | Alataris et al. |
| 8,874,217 B2 | 10/2014 | Alataris et al. |
| 8,874,221 B2 | 10/2014 | Alataris et al. |
| 8,874,222 B2 | 10/2014 | Alataris et al. |
| 8,880,177 B2 | 11/2014 | Alataris et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,892,209 B2 | 11/2014 | Alataris et al. |
| 8,942,808 B2 * | 1/2015 | Peterson ............ A61N 1/36117 606/204 |
| 9,186,504 B2 | 11/2015 | Gross |
| 9,205,258 B2 | 12/2015 | Simon et al. |
| 9,248,279 B2 | 2/2016 | Chen et al. |
| 9,457,186 B2 | 10/2016 | Gross |
| 9,597,521 B2 | 3/2017 | Plotkin et al. |
| 9,656,074 B2 | 5/2017 | Simon et al. |
| 9,713,707 B2 | 7/2017 | Oron et al. |
| 9,764,146 B2 | 9/2017 | Oron et al. |
| 9,782,589 B2 | 10/2017 | Oron et al. |
| 2002/0077554 A1 | 6/2002 | Schwartz et al. |
| 2002/0099419 A1 | 7/2002 | Cohen et al. |
| 2002/0124848 A1 | 9/2002 | Sullivan et al. |
| 2002/0183805 A1 | 12/2002 | Fang et al. |
| 2002/0183817 A1 | 12/2002 | Van Venrooij et al. |
| 2003/0040774 A1 | 2/2003 | Terry et al. |
| 2003/0060858 A1 | 3/2003 | Kieval et al. |
| 2003/0100933 A1 | 5/2003 | Ayal |
| 2003/0114905 A1 | 6/2003 | Kuzma |
| 2003/0176898 A1 | 9/2003 | Gross et al. |
| 2003/0236558 A1 | 12/2003 | Whitehurst et al. |
| 2004/0015205 A1 | 1/2004 | Whitehurst et al. |
| 2004/0019368 A1 | 1/2004 | Lattner et al. |
| 2004/0048795 A1 | 3/2004 | Ivanova et al. |
| 2004/0073270 A1 | 4/2004 | Firlik et al. |
| 2004/0254624 A1 | 6/2004 | Johnson |
| 2004/0167584 A1 | 8/2004 | Carroll et al. |
| 2004/0249431 A1 | 12/2004 | Ransbury et al. |
| 2004/0254612 A1 | 12/2004 | Ezra et al. |
| 2005/0113894 A1 | 5/2005 | Zilberman et al. |
| 2005/0131495 A1 | 6/2005 | Parramon et al. |
| 2005/0143789 A1 | 6/2005 | Whitehurst |
| 2005/0165457 A1 | 7/2005 | Benser et al. |
| 2005/0182457 A1 | 8/2005 | Thrope et al. |
| 2005/0251061 A1 | 11/2005 | Schuler et al. |
| 2006/0085039 A1 | 4/2006 | Hastings et al. |
| 2006/0100668 A1 | 5/2006 | Ben-David et al. |
| 2006/0155345 A1 | 7/2006 | Williams et al. |
| 2006/0271137 A1 | 11/2006 | Stanton-Hicks |
| 2007/0032827 A1 | 2/2007 | Katims |
| 2007/0067000 A1 | 3/2007 | Strother et al. |
| 2007/0067007 A1 | 3/2007 | Schulman |
| 2007/0073353 A1 | 3/2007 | Rooney et al. |
| 2007/0073354 A1 | 3/2007 | Knudson et al. |
| 2007/0083240 A1 | 4/2007 | Peterson et al. |
| 2007/0088397 A1 | 4/2007 | Jacobson |
| 2007/0173893 A1 | 7/2007 | Pitts |
| 2007/0208392 A1 | 9/2007 | Kuschner et al. |
| 2007/0255369 A1 | 11/2007 | Bonde et al. |
| 2007/0293912 A1 | 12/2007 | Cowan et al. |
| 2008/0009914 A1 | 1/2008 | Buysman et al. |
| 2008/0021336 A1 | 1/2008 | Dobak |
| 2008/0027513 A1 | 1/2008 | Carbunaru |
| 2008/0039915 A1 | 2/2008 | Van Den Biggelaar |
| 2008/0065182 A1 | 3/2008 | Strother et al. |
| 2008/0071178 A1 | 3/2008 | Greenland et al. |
| 2008/0103407 A1 | 5/2008 | Bolea et al. |
| 2008/0103572 A1 | 5/2008 | Gerber |
| 2008/0119911 A1 | 5/2008 | Rosero |
| 2008/0132964 A1 | 6/2008 | Cohen et al. |
| 2008/0269740 A1 | 10/2008 | Bonde et al. |
| 2009/0012590 A1 | 1/2009 | Inman et al. |
| 2009/0036975 A1 | 2/2009 | Ward et al. |
| 2009/0048642 A1 | 2/2009 | Goroszeniuk |
| 2009/0149912 A1 | 6/2009 | Dacey et al. |
| 2009/0152954 A1 | 6/2009 | Le et al. |
| 2009/0204170 A1 | 8/2009 | Hastings et al. |
| 2009/0204173 A1 | 8/2009 | Fang et al. |
| 2009/0270951 A1 | 10/2009 | Kallmyer |
| 2009/0281594 A1 | 11/2009 | King et al. |
| 2009/0326602 A1 | 12/2009 | Glukhovsky et al. |
| 2010/0016911 A1 | 1/2010 | Willis et al. |
| 2010/0094367 A1 | 4/2010 | Sen |
| 2010/0121405 A1 | 5/2010 | Ternes et al. |
| 2010/0125310 A1 | 5/2010 | Wilson et al. |
| 2010/0125313 A1 | 5/2010 | Lee et al. |
| 2010/0198298 A1 | 8/2010 | Glukovsky et al. |
| 2010/0211131 A1 | 8/2010 | Williams et al. |
| 2010/0241195 A1 | 9/2010 | Meadows et al. |
| 2010/0249875 A1 | 9/2010 | Kishawi et al. |
| 2010/0312320 A1 | 9/2010 | Faltys et al. |
| 2010/0305392 A1 | 12/2010 | Gross et al. |
| 2010/0324630 A1 | 12/2010 | Lee et al. |
| 2011/0034782 A1 | 2/2011 | Sugimachi et al. |
| 2011/0046696 A1 | 2/2011 | Barolat et al. |
| 2011/0087337 A1 | 4/2011 | Forsell |
| 2011/0093036 A1 | 4/2011 | Mashiach |
| 2011/0112605 A1 | 5/2011 | Fahey |
| 2011/0137365 A1 | 6/2011 | Ben-Erza et al. |
| 2011/0152965 A1 | 6/2011 | Mashiach |
| 2011/0160792 A1 | 6/2011 | Fishel |
| 2011/0160793 A1 | 6/2011 | Gindele |
| 2011/0160798 A1 | 6/2011 | Ackermann et al. |

(56) References Cited

U.S. PATENT DOCUMENTS

| | | |
|---|---|---|
| 2011/0208260 A1 | 8/2011 | Jacobson |
| 2011/0208271 A1 | 8/2011 | Dobak |
| 2011/0224744 A1 | 9/2011 | Moffitt et al. |
| 2011/0230922 A1 | 9/2011 | Fishel |
| 2011/0251660 A1 | 10/2011 | Griswold |
| 2011/0270339 A1 | 11/2011 | Murray et al. |
| 2011/0282412 A1 | 11/2011 | Glukhovsky et al. |
| 2011/0301670 A1 | 12/2011 | Gross |
| 2012/0035679 A1 | 2/2012 | Dagan et al. |
| 2012/0041511 A1 | 2/2012 | Lee |
| 2012/0041514 A1 | 2/2012 | Gross et al. |
| 2012/0065701 A1 | 3/2012 | Cauller |
| 2012/0083857 A1 | 4/2012 | Bradley et al. |
| 2012/0101326 A1 | 4/2012 | Simon et al. |
| 2012/0123498 A1 | 5/2012 | Gross |
| 2012/0130448 A1 | 5/2012 | Woods et al. |
| 2012/0130463 A1 | 5/2012 | Ben-David et al. |
| 2012/0158081 A1 | 6/2012 | Gross et al. |
| 2012/0215285 A1 | 8/2012 | Tahmasian et al. |
| 2012/0296389 A1 | 11/2012 | Fang et al. |
| 2013/0006326 A1 | 1/2013 | Ackermann et al. |
| 2013/0066393 A1 | 3/2013 | Gross et al. |
| 2013/0325081 A1 | 12/2013 | Karst et al. |
| 2013/0325084 A1 | 12/2013 | Lee |
| 2014/0214134 A1 | 7/2014 | Peterson |
| 2014/0296940 A1 | 10/2014 | Gross |
| 2015/0004709 A1 | 1/2015 | Nazarpoor |
| 2015/0018728 A1 | 1/2015 | Gross et al. |
| 2015/0039046 A1 | 2/2015 | Gross |
| 2015/0080979 A1 | 3/2015 | Lasko et al. |
| 2015/0100109 A1 | 4/2015 | Feldman et al. |
| 2015/0148861 A1 | 5/2015 | Gross |
| 2015/0148878 A1 | 5/2015 | Yoo et al. |
| 2015/0174406 A1 | 6/2015 | Lamensdorf et al. |
| 2015/0258339 A1 | 9/2015 | Burchiel et al. |
| 2015/0335882 A1 | 11/2015 | Gross et al. |
| 2016/0206882 A1 | 7/2016 | Oron et al. |
| 2016/0206889 A1 | 7/2016 | Plotkin et al. |
| 2016/0206890 A1 | 7/2016 | Oron et al. |
| 2016/0361544 A1 | 12/2016 | Oron et al. |
| 2017/0007829 A1 | 1/2017 | Gross |
| 2017/0128724 A1 | 5/2017 | Oron et al. |
| 2017/0136232 A1 | 5/2017 | Oron et al. |
| 2017/0224996 A1 | 8/2017 | Oron et al. |
| 2017/0296426 A1 | 10/2017 | Oron et al. |

FOREIGN PATENT DOCUMENTS

| | | | |
|---|---|---|---|
| EP | 1533000 | 5/2005 | |
| WO | 1998/010832 | 3/1998 | |
| WO | 1999/026530 | 6/1999 | |
| WO | 01/10432 | 2/2001 | |
| WO | 2001/010375 | 2/2001 | |
| WO | 01/26729 | 4/2001 | |
| WO | 02/09808 | 2/2002 | |
| WO | 2004/064729 | 8/2004 | |
| WO | 2006/102626 | 9/2006 | |
| WO | 2007/019491 | 2/2007 | |
| WO | 2009/055574 | 4/2009 | |
| WO | 2009/110935 | 9/2009 | |
| WO | 2011/154937 | 12/2011 | |
| WO | 2012/012591 | 1/2012 | |
| WO | 2013/106884 | 7/2013 | |
| WO | 2013/111137 | 8/2013 | |
| WO | WO 2013111137 A2 * | 8/2013 | ............ A61N 5/022 |
| WO | 2013/156038 | 10/2013 | |
| WO | 2014/068577 A2 | 5/2014 | |
| WO | 2014/068577 A3 | 5/2014 | |
| WO | 2014/081978 | 5/2014 | |
| WO | 2014/087337 | 6/2014 | |
| WO | 2014/167568 | 10/2014 | |
| WO | 2015/004673 | 1/2015 | |
| WO | 2016/172109 | 10/2016 | |

OTHER PUBLICATIONS

D.W. Eisele, A.R. Schwartz, and P.L. Smith, "Tongue neuromuscular and direct hypoglossal nerve stimulation for obstructive sleep apnea.," Otolaryngologic clinics of North America, vol. 36, 2003, p. 501.

G.E. Loeb, F.J.R. Richmond, J. Singh, R.A. Peck, W. Tan, Q. Zou, and N. Sachs, "RF-powered BIONs™ for stimulation and sensing," Engineering in Medicine and Biology Society, 2004. IEMBS'04. 26th Annual International Conference of the IEEE, 2005, pp. 4182-4185.

G.E. Loeb, F.J. Richmond, and L.L. Baker, "The BION devices: injectable interfaces with peripheral nerves and muscles," Neurosurgical focus, vol. 20, 2006, pp. 1-9.

E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.

A. Oliven, R.P. Schnall, G. Pillar, N. Gavriely, and M. Odeh, "Sublingual electrical stimulation of the tongue during wakefulness and sleep," Respiration physiology, vol. 127, 2001, pp. 217-226.

A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023.

A. Oliven, M. Odeh, L. Geitini, R. Oliven, U. Steinfeld, A.R. Schwartz, and N. Tov, "Effect of coactivation of tongue protrusor and retractor muscles on pharyngeal lumen and airflow in sleep apnea patients," Journal of Applied Physiology, vol. 103, 2007, p. 1662.

A.R. Schwartz, D.W. Eisele, A. Hari, R. Testerman, D. Erickson, and P.L. Smith, "Electrical stimulation of the lingual musculature in obstructive sleep apnea," Journal of Applied Physiology, vol. 81, 1996, p. 643.

W.H. Tran, G.E. Loeb, F.J.R. Richmond, A.C. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.

W.H. Tran, G.E. Loeb, F.J.R. Richmond, R. Ahmed, G.T. Clark, and P.B. Haberman, "First subject evaluated with simulated BION™ treatment in genioglossus to prevent obstructive sleep apnea," Engineering in Medicine and Biology Society, 2004. IEMBS'04. 26th Annual International Conference of the IEEE, 2005, pp. 4287-4289.

P.R. Troyk, "Injectable electronic identification, monitoring, and stimulation systems," Biomedical Engineering, vol. 1, 1999, p. 177.

T.K. Whitehurst, J.H. Schulman, K.N. Jaax, and R. Carbunaru, "The Bion® Microstimulator and its Clinical Applications," Implantable Neural Prostheses 1, 2009, pp. 253-273.

D.J. Young, "Wireless powering and data telemetry for biomedical implants," Engineering in Medicine and Biology Society, 2009. EMBC 2009. Annual International Conference of the IEEE, 2009, pp. 3221-3224.

Reid R. Harrison, et al., "Wireless Neural Recording with Single Low-Power Integrated Circuit", IEEE Trans Neural Syst Rehabil Eng. Aug. 2009; 17(4): 322-329.

An International Search Report which issued during the prosecution and a Written Opinion both dated Apr. 17, 2012 which issued during the prosecution of Applicant's PCT/IL11/00870.

Patents Galore: Implantable Neurostimulators Fight Snoring and Corpse Eye-Proof Scanners. Printout from http://medgadget.com/2006/03/patents_galore.html (Downloaded Jan. 2012).

Chris Seper, "Neuros Medical Launches to Develop New Device to Block Amputee, Chronic Pain", Mar. 16, 2009.

Urgent® PC, Simple. Safe. Effective. Neuromodulation System, Uroplasty, Mar. 2009.

"JumpStart and Case Technology Ventures Invest in Neuros Medical", CTV Case Technology Ventures, Mar. 17, 2009.

(56) References Cited

OTHER PUBLICATIONS

"Responses to median and tibial nerve stimulation in patients with chronic neuropathic pain", by Theuvenet, Brain Topography, vol. 11, No. 4, 1999, pp. 305-313(9)—an abstract.
Armstrong, J, "Is electrical stimulation effective in reducing neuropathic pain in patients with diabetes?", by Foot Ankle Surg. Jul.-Aug. 1997; 36(4): 260-3—an abstract.
Ross Davis, Cerebellar Stimulation for Cerebral Palsy Spasticity, Function and Seizures. Clinical Neuroscience Center, 1999. pp. 290-299.
An Office Action dated Feb. 13, 2004, which issued during the prosecution of U.S. Appl. No. 10/254,024.
Bathien et al., Inhibition and synchronisation of tremor induced by a muscle twitch. J. Neurol, Neurosurg. And Psych. 1980, 43, 713-718.
Jobges et al., Vibratory proprioceptive stimulation affects Parkinsonian tremor. Parkinsonism & Related Disorders, 8(3), 171-176, Jan. 2002.
Mones and Weiss, The response of the tremor of patients with Parkinsonism to peripheral nerve stimulation. J. Neurol. Neurosurg. Psychiat. 1969, 32. 512-519.
Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.
An Office Action dated May 19, 2017, which issued during the prosecution of U.S. Appl. No. 14/935,941.
M. Manfredi, "Differential Block of conduction of larger fibers in peripheral nerve by direct current", Arch. Ital. Biol. 108:52-71, 1970.
A Restriction Requirement dated May 11, 2012, which issued during the prosecution of U.S. Appl. No. 12/946,246.
Cerebral Palsy, Barry S. Russman MD, CCurrent Science Inc. 2000.
A Notice of Allowance dated Mar. 7, 2005, which issued during the prosecution of U.S. Appl. No. 10/254,024.
A Notice of Allowance dated Aug. 26, 2004, which issued during the prosecution of U.S. Appl. No. 10/254,024.
An Office Action dated Jun. 24, 2011, which issued during the prosecution of U.S. Appl. No. 12/796,102.
An International Search Report and a Written Opinion both dated Nov. 14, 2011, which issued during the prosecution of Applicant's PCT/IL2011/000440.
An International Preliminary Report on Patentability dated Dec. 10, 2012, which issued during the prosecution of Applicant's PCT/IL2011/000440.
U.S. Appl. No. 60/263,834, filed Jan. 2, 2001.
Sweeney JD et al., "An asymmetric two electrode cuff for generation of unidirectionally propagated action potentials," IEEE Transactions on Biomedical Engineering, vol. BME-33(6) (1986).
An Office Action dated Apr. 9, 2012, which issued during the prosecution of U.S. Appl. No. 12/796,102.
Invitation to pay Additional Fees dated May 10, 2013 which issued during the PCT/IL2013/050069.
Naples GG et al., "A spiral nerve cuff electrode for peripheral nerve stimulation," by IEEE Transactions on Biomedical Engineering, 35(11) (1988).
Sweeney JD et al., "A nerve cuff technique for selective excitation of peripheral nerve trunk regions," IEEE Transactions on Biomedical Engineering, 37(7) (1990).
Ungar IJ et al., "Generation of unidirectionally propagating action potentials using a monopolar electrode cuff," Annals of Biomedical Engineering, 14:437-450 (1986).
Fitzpatrick et al., in "A nerve cuff design for the selective activation and blocking of myelinated nerve fibers," Ann. Conf. of the IEEE Eng. in Medicine and Biology Soc, 13(2), 906 (1991).
Rijkhoff NJ et al., "Orderly recruitment of motoneurons in an acute rabbit model," Ann. Conf. of the IEEE Eng., Medicine and Biology Soc., 20(5):2564 (1998).
Van den Honert C et al., "A technique for collision block of peripheral nerve: Frequency dependence," MP-12, IEEE Trans. Biomed. Eng. 28:379-382 (1981).

Baratta R et al., "Orderly stimulation of skeletal muscle motor units with tripolar nerve cuff electrode," IEEE Transactions on Biomedical Engineering, 36(8):836-43 (1989).
Notice of Allowance dated Sep. 1, 2017, which issued during the prosecution of U.S. Appl. No. 14/649,873.
An Office Action dated Apr. 4, 2017, which issued during the prosecution of U.S. Appl. No. 14/601,604.
European Search Report dated Mar. 10, 2017, which issued during the prosecution of Applicant's European App No. 16196864.9.
An Office Action dated Dec. 5, 2013, which issued during the prosecution of U.S. Appl. No. 13/528,433.
An Office Action dated Sep. 30, 2013, which issued during the prosecution of U.S. Appl. No. 12/796,102.
An Office Action dated Feb. 27, 2017, which issued during the prosecution of U.S. Appl. No. 14/649,873.
Notice of Allowance dated Jun. 13, 2017, which issued during the prosecution of U.S. Appl. No. 14/735,741.
European Search Report dated Feb. 3, 2017, which issued during the prosecution of Applicant's European App No. 16196878.9.
Notice of Allowance dated Jun. 2, 2017, which issued during the prosecution of U.S. Appl. No. 14/735,741.
An Office Action dated Nov. 21, 2016, which issued during the prosecution of U.S. Appl. No. 14/601,626.
An Office Action dated Aug. 8, 2017, which issued during the prosecution of U.S. Appl. No. 14/735,741.
An Office Action dated Dec. 12, 2016, which issued during the prosecution of U.S. Appl. No. 14/939,418.
Brindley (1983) A technique for anodally blocking large nerve fibers.
DJOGlobal.com—Interferential Current Therapy (IFC).
U.S. Appl. No. 60/985,353, filed Nov. 5, 2007.
electrotherapy.org—Interferential Therapy.
Lind (2012) Advances in spinal cord stimulation.
Physical Therapy Web.com—Interferential Current (IFC) Equipment.
Shealy (1967) Electrical inhibition of pain by stimulation of the dorsal columns.
Nov. 30, 2015 massdevice.com—St. Jude Medical's Proclaim Elite debuts in Europe.
Kaplan et al. (2009) Design and fabrication of an injection tool for neuromuscular microstimulators.
Supplementary European Search Report dated Dec. 22, 2014, which issued during the prosecution of Applicant's European App No. 11792044.7.
An Office Action dated Oct. 30, 2015, which issued during the prosecution of U.S. Appl. No. 14/226,723.
An Office Action dated Apr. 5, 2017, which issued during the prosecution of U.S. Appl. No. 14/374,375.
Kucklick, Theodore R., ed. *The medical device R&D handbook*. Chapter 3—Intro to needles and cannulae. CRC Press, 2012.
Reggiani et al. "Biophysical effects of high frequency electrical field on muscle fibers in culture." (2009) pp. 49-56.
UCLA Team Reports Initial Success with Trigeminal Nerve Stimulation epilepsy. https://web.archive.org/web/20121020145122/https://www.epilepsy.com/newsletter/apr09_STIM.
Szmurlo, R., Starzynski, J., Wincenciak, S. and Rysz, A. (2009) 'Numerical model of vagus nerve electrical stimulation', *COMPEL—The international journal for computation and mathematics in electrical and electronic engineering*, 28(1), pp. 211-220.
Sinan Filiz, Luke Xie, Lee E. Weiss, O.B. Ozdoganlar, Micromilling of microbarbs for medical implants, International Journal of Machine Tools and Manufacture, vol. 48 Issues 3-4, Mar. 2008, pp. 459-472.
Hagblad, Jimmie. Non-invasive techniques for assessment of peripheral blood flow at different vascular depths. Diss. Mälardalen University, 2011.
An Office Action dated Dec. 26, 2017, which issued during the prosecution of U.S. Appl. No. 14/935,941.
An Office Action dated Jan. 8, 2018, which issued during the prosecution of U.S. Appl. No. 14/935,941.
An Office Action dated Mar. 5, 2018, which issued during the prosecution of U.S. Appl. No. 15/360,501.

\* cited by examiner

IMPLANTABLE ELECTROSTIMULATOR FOR IMPROVING BLOOD FLOW

CROSS-REFERENCES

The present application is a Continuation of U.S. patent application Ser. No. 14/735,741 to Oron et al., filed Jun. 10, 2015, and entitled "Implantable electrostimulator for improving blood flow," which published as US 2016/0361544 (now U.S. Pat. No. 9,782,589).

FIELD OF THE INVENTION

Some applications of the invention relate in general to implantable electrostimulators. More specifically, some applications of the present invention relate to improving blood flow using implantable electrostimulators.

BACKGROUND

Peripheral artery occlusive disease (PAOD) (also known as peripheral artery disease, peripheral vascular disease, and peripheral obliterative arteriopathy) is a condition in which peripheral arteries (i.e., arteries except those that supply the heart or the brain) are narrowed. PAOD is associated with diabetes, smoking, hypertension, and hypercholesterolemia, and is often the result of atherosclerosis. PAOD affects over 200 million people worldwide.

SUMMARY OF THE INVENTION

An electrostimulator implant is implanted in a subject that has, or is at risk of developing, peripheral artery occlusive disease (PAOD). For some applications, the implant comprises a detector that detects a factor indicative of local blood supply in the tissue of a limb in which the implant is implanted. For some applications, an extracorporeal device is attached to the limb, and provides wireless power, processing power, and/or additional sensors.

There is therefore provided, in accordance with an application of the present invention, apparatus, including:
an electrostimulator-implant, percutaneously advanceable into tissue of a limb of a subject, and including:
an intracorporeal sensor, configured to detect a factor indicative of local blood supply in the tissue of the limb;
an electrode disposed at an outer surface of the implant;
an antenna, configured to wirelessly receive power; and
circuitry, powered by the received power, and configured to drive the electrode to apply a bloodflow-increasing current to the tissue at least in part responsively to the detected factor.

In an application, the intracorporeal sensor includes a temperature sensor, configured to detect a temperature of the tissue.

In an application, the intracorporeal sensor includes an oximeter, configured to detect an oxygen saturation of the tissue.

In an application, the intracorporeal sensor includes a pressure sensor, configured to detect a pressure within the tissue.

In an application, the intracorporeal sensor includes an accelerometer, configured to detect movement indicative of expansion of an artery of the limb.

In an application, the bloodflow-increasing current has a frequency of 1-100 Hz, and the circuitry is configured to drive the electrode to apply the 1-100 Hz bloodflow-increasing current to the tissue at least in part responsively to the detected movement.

In an application, the apparatus further includes an extracorporeal device, attachable to the limb, and configured:
to wirelessly transmit the power received by the antenna,
to receive from the implant information regarding the detected factor, and
at least in part responsively to the received information, to wirelessly drive the circuitry to drive the electrode to apply the bloodflow-increasing current.

In an application, the extracorporeal device includes an extracorporeal sensor, configured to detect a factor indicative of local blood supply in the tissue of the limb, and the extracorporeal device is configured to wirelessly drive the circuitry to drive the electrode to apply the bloodflow-increasing current to the tissue, at least in part responsively to (i) the factor detected by the intracorporeal sensor, and (ii) the factor detected by the extracorporeal sensor.

In an application, the extracorporeal sensor includes a temperature sensor, configured to detect a temperature of the tissue.

In an application, the extracorporeal sensor includes an oximeter, configured to detect an oxygen saturation of the limb.

In an application, the extracorporeal sensor includes a pressure sensor, configured to detect a pressure within the limb.

In an application, the extracorporeal sensor includes an accelerometer, configured to detect movement indicative of expansion of an artery of the limb.

In an application, the extracorporeal device includes an extracorporeal accelerometer, configured to detect movement of the limb, and the extracorporeal device is configured to wirelessly drive the circuitry to drive the electrode to apply the bloodflow-increasing current to the tissue, at least in part responsively to (i) the factor detected by the intracorporeal sensor, and (ii) the movement detected by the extracorporeal accelerometer.

In an application, the extracorporeal device includes an extracorporeal temperature sensor, configured to detect an ambient temperature, and the extracorporeal device is configured to wirelessly drive the circuitry to drive the electrode to apply the bloodflow-increasing current to the tissue, at least in part responsively to (i) the factor detected by the intracorporeal sensor, and (ii) the ambient temperature detected by the extracorporeal temperature sensor.

In an application, the extracorporeal device is configured to alternate between (i) a first mode in which the extracorporeal device wirelessly drives the circuitry to drive the electrode to apply the bloodflow-increasing current, the bloodflow-increasing current having a frequency of 1-100 Hz, and (ii) a second mode in which the extracorporeal device wirelessly drives the circuitry to apply a second electrical current having a frequency of 1-10 kHz.

There is further provided, in accordance with an application of the present invention, apparatus, including:
an electrostimulator-implant, percutaneously advanceable into tissue of a limb of a subject, and including:
a temperature sensor, configured to detect a temperature of the tissue;
an electrode disposed at an outer surface of the implant;
an antenna, configured to wirelessly receive power; and
circuitry, powered by the received power, and configured to drive the electrode to apply a bloodflow-increasing current to the tissue at least in part responsively to the detected temperature.

In an application, the bloodflow-increasing current has a frequency of 1-100 Hz, and the circuitry is configured to drive the electrode to apply the 1-100 Hz bloodflow-increasing current to the tissue at least in part responsively to the detected temperature.

In an application, the circuitry is configured to drive the electrode to apply the bloodflow-increasing current in response to the detected temperature being below a threshold temperature.

In an application, the apparatus further includes an extracorporeal device, attachable to the limb, and configured to wirelessly transmit the power received by the antenna.

In an application, the extracorporeal device is configured:
  to wirelessly drive the temperature sensor,
  to receive from the implant information regarding the detected temperature, and
  at least in part responsively to the received information, to wirelessly drive the circuitry to drive the electrode to apply the bloodflow-increasing current.

In an application, the temperature sensor is a first temperature sensor, the extracorporeal device includes a second temperature sensor, and the extracorporeal device is configured to wirelessly drive the circuitry to drive the electrode to apply the bloodflow-increasing current to the tissue, at least in part responsively to (i) the temperature detected by the first temperature sensor, and (ii) a temperature detected by the second temperature sensor.

In an application, the extracorporeal device is configured to alternate between (i) a first mode in which the extracorporeal device wirelessly drives the circuitry to drive the electrode to apply a first electrical current having a frequency of 1-100 Hz, and (ii) a second mode in which the extracorporeal device wirelessly drives the circuitry to apply a second electrical current having a frequency of 1-10 kHz.

In an application, the implant further includes a pressure sensor, configured to detect a pressure within the tissue, and the circuitry is configured to drive the electrode to apply the current at least in part responsively to the detected pressure.

In an application, the pressure includes a pulse pressure, and the circuitry is configured to drive the electrode to apply the current at least in part responsively to the detected pulse pressure.

There is further provided, in accordance with an application of the present invention, apparatus, including:
  an electrostimulator-implant, percutaneously advanceable into tissue of a limb of a subject, and including:
    an oximeter, configured to detect an oxygen saturation of the tissue;
    an electrode disposed at an outer surface of the implant;
    an antenna, configured to wirelessly receive power; and
    circuitry, powered by the received power, and configured to drive the electrode to apply a bloodflow-increasing current to the tissue at least in part responsively to the detected oxygen saturation.

In an application, the circuitry is configured to drive the electrode to apply the bloodflow-increasing current in response to the detected oxygen saturation being below a threshold oxygen saturation.

In an application, the bloodflow-increasing current has a frequency of 1-100 Hz, and the circuitry is configured to drive the electrode to apply the 1-100 Hz bloodflow-increasing current to the tissue at least in part responsively to the detected oxygen saturation.

In an application, the apparatus further includes an extracorporeal device, attachable to the limb, and configured to wirelessly transmit the power received by the antenna.

In an application, the extracorporeal device is configured:
  to wirelessly drive the oximeter,
  to receive from the implant information regarding the detected oxygen saturation, and
  at least in part responsively to the received information, to wirelessly drive the circuitry to drive the electrode to apply the bloodflow-increasing current.

In an application, the oximeter is a first oximeter, the extracorporeal device includes a second oximeter, and the extracorporeal device is configured to wirelessly drive the circuitry to drive the electrode to apply the bloodflow-increasing current to the tissue, at least in part responsively to (i) the oxygen saturation detected by the first oximeter, and (ii) an oxygen saturation detected by the second oximeter.

In an application, the extracorporeal device is configured to alternate between (i) a first mode in which the extracorporeal device wirelessly drives the circuitry to drive the electrode to apply a first electrical current having a frequency of 1-100 Hz, and (ii) a second mode in which the extracorporeal device wirelessly drives the circuitry to apply a second electrical current having a frequency of 1-10 kHz.

In an application, the implant further includes a pressure sensor, configured to detect a pressure within the tissue, and the circuitry is configured to drive the electrode to apply the current at least in part responsively to the detected pressure.

In an application, the detected pressure includes a pulse pressure, and the circuitry is configured to drive the electrode to apply the current at least in part responsively to the detected pulse pressure.

There is further provided, in accordance with an application of the present invention, apparatus, including:
  an electrostimulator-implant, percutaneously advanceable into tissue of a limb of a subject, and including:
    a pressure sensor, configured to detect a pressure within the tissue;
    an electrode disposed at an outer surface of the implant;
    an antenna, configured to wirelessly receive power; and
    circuitry, powered by the received power, and configured to drive the electrode to apply a bloodflow-increasing current to the tissue at least in part responsively to the detected pressure.

In an application, the detected pressure includes a pulse pressure, and the circuitry is configured to drive the electrode to apply the current at least in part responsively to the detected pulse pressure.

In an application, the bloodflow-increasing current has a frequency of 1-100 Hz, and the circuitry is configured to drive the electrode to apply the 1-100 Hz bloodflow-increasing current to the tissue at least in part responsively to the detected pressure.

In an application, the apparatus further includes an extracorporeal device, attachable to the limb, and configured to wirelessly transmit the power received by the antenna.

In an application, the extracorporeal device is configured:
  to wirelessly drive the pressure sensor,
  to receive from the implant information regarding the detected pressure, and
  at least in part responsively to the received information, to wirelessly drive the circuitry to drive the electrode to apply the bloodflow-increasing current.

In an application, the pressure sensor is a first pressure sensor, the extracorporeal device includes a second pressure sensor, and the extracorporeal device is configured to wirelessly drive the circuitry to drive the electrode to apply the bloodflow-increasing current to the tissue, at least in part responsively to (i) the pressure detected by the first pressure sensor, and (ii) a pressure detected by the second pressure sensor.

In an application, the extracorporeal device is configured to alternate between (i) a first mode in which the extracorporeal device wirelessly drives the circuitry to drive the electrode to apply a first electrical current having a frequency of 1-100 Hz, and (ii) a second mode in which the extracorporeal device wirelessly drives the circuitry to apply a second electrical current having a frequency of 1-10 kHz.

There is further provided, in accordance with an application of the present invention, apparatus, including:

an electrostimulator-implant, percutaneously advanceable into tissue of a limb of a subject, and including:
an accelerometer, configured to detect movement indicative of expansion of an artery of the limb;
an electrode disposed at an outer surface of the implant;
an antenna, configured to wirelessly receive power; and
circuitry, powered by the received power, and configured to drive the electrode to apply a bloodflow-increasing current to the tissue at least in part responsively to the detected movement.

In an application, the circuitry is configured to drive the electrode to apply the bloodflow-increasing current in response to a magnitude of the detected movement being below a threshold magnitude.

In an application, the bloodflow-increasing current has a frequency of 1-100 Hz, and the circuitry is configured to drive the electrode to apply the 1-100 Hz bloodflow-increasing current to the tissue at least in part responsively to the detected movement.

In an application, the apparatus further includes an extracorporeal device, attachable to the limb, and configured to wirelessly transmit the power received by the antenna.

In an application, the extracorporeal device is configured:
to wirelessly drive the accelerometer,
to receive from the implant information regarding the detected movement, and
at least in part responsively to the received information, to wirelessly drive the circuitry to drive the electrode to apply the bloodflow-increasing current.

In an application, the accelerometer is a first accelerometer, the extracorporeal device includes a second accelerometer, and the extracorporeal device is configured to wirelessly drive the circuitry to drive the electrode to apply the bloodflow-increasing current to the tissue, at least in part responsively to (i) the movement detected by the first accelerometer, and (ii) a movement detected by the second accelerometer.

In an application, the extracorporeal device is configured to alternate between (i) a first mode in which the extracorporeal device wirelessly drives the circuitry to drive the electrode to apply a first electrical current having a frequency of 1-100 Hz, and (ii) a second mode in which the extracorporeal device wirelessly drives the circuitry to apply a second electrical current having a frequency of 1-10 kHz.

In an application, the implant further includes a pressure sensor, configured to detect a pressure within the tissue, and the circuitry is configured to drive the electrode to apply the current at least in part responsively to the detected pressure.

In an application, the detected pressure includes a pulse pressure, and the circuitry is configured to drive the electrode to apply the current at least in part responsively to the detected pulse pressure.

There is further provided, in accordance with an application of the present invention, a method of treating a subject, the method including:

identifying the subject as having peripheral arterial occlusive disease (PAOD); and
in response to the identifying:
percutaneously implanting an electrostimulator implant in a limb of the subject; and
increasing blood flow in the limb by activating the implant such that the implant applies an electrical current to the limb.

In an application, the method further includes repositioning the implant within the limb at least in part responsively to a blood-flow change induced by the activating of the implant.

In an application, the method further includes calibrating the implant at least in part responsively to a blood-flow change induced by the activating of the implant.

In an application, identifying the subject includes identifying the subject as not suffering from peripheral polyneuropathy.

In an application, activating the implant includes activating the implant without inducing paresthesia.

In an application, activating the implant includes activating the implant such that it applies to the limb an electrical current having a frequency of 1-100 Hz.

In an application, activating the implant includes activating the implant to alternate between a first mode in which the implant applies a first electrical current having a frequency of 1-100 Hz, and a second mode in which the implant applies a second electrical current having a frequency of 1-10 kHz.

In an application, activating the implant includes activating the implant such that (i) the implant increases the blood flow in the limb by applying the first electrical current to the limb, and (ii) the implant induces relieves pain by applying the second electrical current to the limb.

In an application, the method further includes repositioning the implant within the limb at least in part responsively to a blood-flow change induced by the activating of the implant.

In an application, the method further includes repositioning the implant within the limb at least in part responsively to a level of pain relief induced by the activating of the implant.

In an application, the method further includes repositioning the implant within the limb at least in part responsively to a level of paresthesia induced by the activating of the implant.

In an application, the method further includes:
identifying (a) a blood-flow change induced by the activating of the implant and (b) a level of pain relief induced by the activating of the implant; and
repositioning the implant within the limb at least in part responsively to (a) and (b).

In an application, the method further includes:
identifying (a) a blood-flow change induced by the activating of the implant and (b) a level of paresthesia induced by the activating of the implant; and
repositioning the implant within the limb at least in part responsively to (a) and (b).

In an application, the method further includes calibrating the implant at least in part responsively to a blood-flow change induced by the activating of the implant.

In an application, the method further includes calibrating the implant at least in part responsively to a level of pain relief induced by the activating of the implant.

In an application, the method further includes calibrating the implant at least in part responsively to a level of paresthesia induced by the activating of the implant.

In an application, the method further includes:

identifying (a) a blood-flow change induced by the activating of the implant and (b) a level of pain relief induced by the activating of the implant; and calibrating the implant at least in part responsively to (a) and (b).

In an application, the method further includes:

identifying (a) a blood-flow change induced by the activating of the implant and (b) a level of paresthesia induced by the activating of the implant; and calibrating the implant at least in part responsively to (a) and (b).

In an application, activating the implant includes activating the implant to alternate between being in the first mode for 1-30 minutes, and being in the second mode for 1-10 minutes.

In an application, the step of identifying includes (i) receiving infrared emission information, and (ii) identifying the subject as having PAOD at least in part responsively to the infrared emission information.

In an application, the method further includes repositioning the implant within the limb at least in part responsively to an infrared-emission change induced by the activating of the implant.

In an application, the method further includes calibrating the implant at least in part responsively to an infrared-emission change induced by the activating of the implant.

In an application, receiving the infrared emission information includes receiving a thermographic image of the subject.

In an application, the step of identifying includes (i) receiving temperature information, and (ii) identifying the subject as having PAOD at least in part responsively to the temperature information.

In an application, the method further includes repositioning the implant within the limb at least in part responsively to a temperature change induced by the activating of the implant.

In an application, the method further includes calibrating the implant at least in part responsively to a temperature change induced by the activating of the implant.

In an application, the step of identifying includes (i) receiving Doppler information, and (ii) identifying the subject as having PAOD at least in part responsively to the Doppler information.

In an application, the method further includes repositioning the implant within the limb at least in part responsively to a Doppler change induced by the activating of the implant.

In an application, the method further includes calibrating the implant at least in part responsively to a Doppler change induced by the activating of the implant.

In an application, implanting the electrostimulator in the limb includes implanting the electrostimulator in a leg of the subject.

In an application, implanting the electrostimulator in the leg includes implanting the electrostimulator within 10 mm of a tibial nerve of the subject.

In an application, activating the implant includes activating the implant such that it applies an electrical current to the tibial nerve.

There is further provided, in accordance with an application of the present invention, apparatus for treating a subject, the apparatus including:

an implant, including:
an injectable housing,
an electrode disposed on an outer surface of the housing,
circuitry, configured to alternate between:

(i) a first mode in which the circuitry drives the electrode to apply a first electrical current having a frequency of 1-100 Hz, and (ii) a second mode in which the implant applies a second electrical current having a frequency of 1-10 kHz; and an introducer:
including a tube defining a lumen, the tube being percutaneously-advanceable into the subject, and the lumen dimensioned to at least temporarily house the implant, and configured to deploy the implant from a distal end of the lumen by moving the implant and the distal end of the lumen relative to each other.

The present invention will be more fully understood from the following detailed description of applications thereof, taken together with the drawings, in which:

DETAILED DESCRIPTION OF EMBODIMENTS

Figure 1:
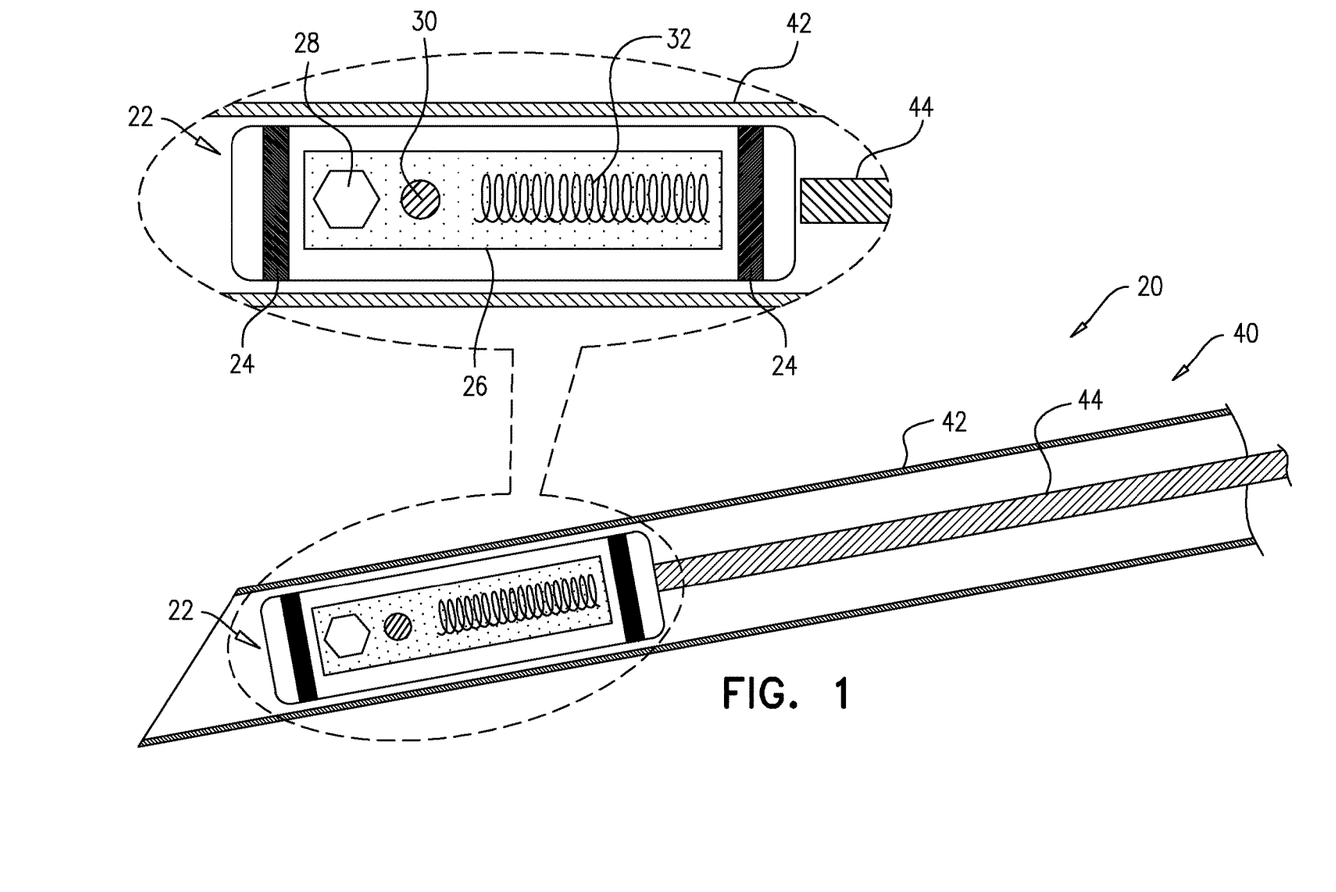
FIG. 1 is a schematic illustration of a system comprising an implant and an introducer, in accordance with some applications of the invention.

Reference is made to FIG. 1, which is a schematic illustration of a system 20 comprising an implant 22 and an introducer 40, in accordance with some applications of the invention.

Implant 22 comprises one or more tissue-contacting electrodes 24 disposed at an outer surface of the implant, and circuitry 26 configured to drive the electrodes to apply a treatment current to tissue that is in contact with the electrodes (e.g., circuitry 26 defines and/or comprises a control unit 28). Implant 22 comprises a battery 30, or an antenna 32, or both. For some applications, implant 22 comprises a power source, such as a primary battery, and does not comprise an antenna. For some applications, antenna 32 is configured to receive wireless power. For some such applications, the received wireless power is used by circuitry 26 to recharge battery 30. For some such applications, the received wireless power is used by circuitry 26 to immediately (e.g., within 1 second of receiving the wireless power) drive electrodes 24 to apply the treatment current. For example, implant 22 may not comprise battery 30 or another non-transient power source (although the implant may comprise a capacitor).

Introducer 40 comprises a tube 42 that defines a lumen and is percutaneously-advanceable into a subject. The lumen of tube 42 is dimensioned to house implant 22 at least temporarily. Introducer 40 is configured to deploy the implant from a distal end of the lumen by moving the implant and the distal end of the lumen relative to each other. For example, once implant 22 is disposed inside the subject, within a distal portion of the introducer, tube 42 may be withdrawn proximally while a reference-force rod 44, reversibly coupled to the implant, and slidable with respect to tube 42, holds the implant stationary by providing a reference force to the implant. Alternatively, rod 44 may push implant 22 out of the distal end of tube 42 while the tube is maintained stationary.

Typically, implant 22 has a transverse cross-sectional area (i.e., transverse to the longitudinal axis of the implant along which the implant is injected) of 0.5-8 mm^2 (e.g., 1-4 mm^2).

Figure 2:
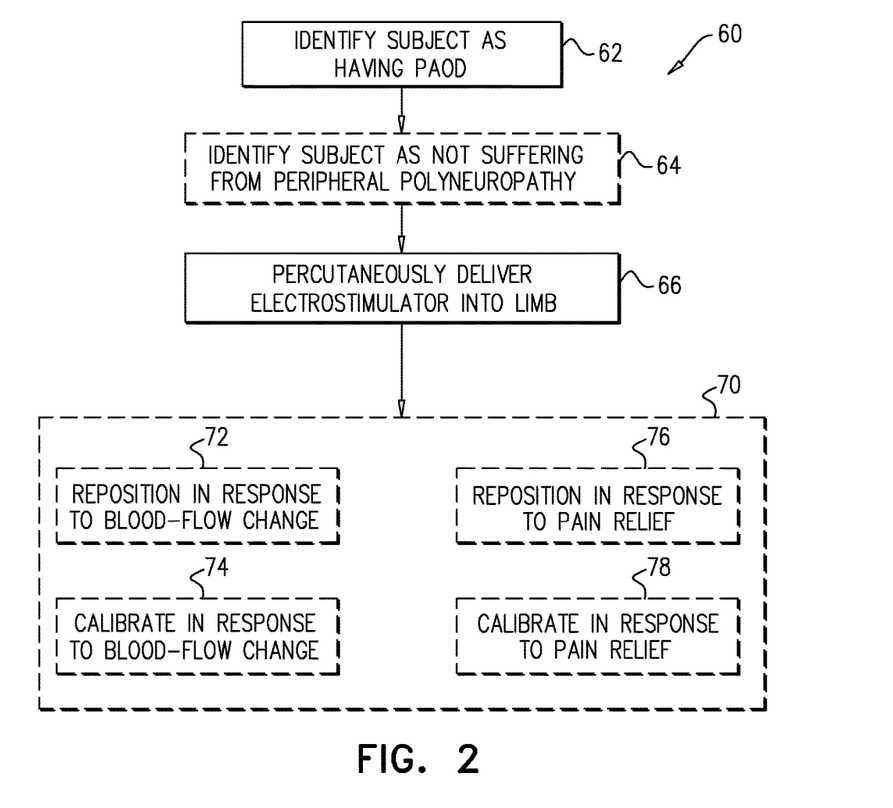
FIG. 2 is a flow chart showing at least some steps in a technique for treating a subject, in accordance with some applications of the invention.

Reference is made to FIG. 2, which is a flow chart showing at least some steps in a technique 60 for treating a subject, in accordance with some applications of the invention. A subject is identified as having peripheral artery occlusive disease (PAOD) (step 62).

Typically, the subject has been previously diagnosed with PAOD (e.g., independently and/or elsewhere), and step 62 is performed by inspecting the medical records of the subject. Alternatively, step 62 may comprise one or more diagnostic techniques. For some applications, the identification of the subject as having PAOD is performed using infrared emission information, e.g., based on infrared emission from a limb of the subject. For example, thermographic imaging or an infrared thermometer may be used. For some applications, the identification of the subject as having PAOD is performed by measuring the temperature of a limb of the subject using contact-based techniques. For some applications, the identification of the subject as having PAOD is performed using Doppler information that is indicative of blood flow in a limb of the subject. For some applications, ultrasound or laser technologies may be used to identify PAOD. For some applications, transcutaneous oximetry is used to identify the subject as having PAOD.

In response to the identification of the subject as having PAOD, an electrostimulator implant (e.g., implant 22) is percutaneously delivered into (e.g., implanted in) a limb of the subject (step 66).

The implant is activated such that the implant applies an electrical current to the limb. The step of activating the implant is not shown in the flowchart of FIG. 2 because activation may be performed before, during or after implantation.

Circuitry 26 (e.g., control unit 28) of implant 22 is typically configured to configure the treatment current to have a frequency of below 100 Hz (e.g., 1-100 Hz). For example, the treatment current may have a frequency of 1-10 Hz (e.g., 2-5 Hz), 7-12 Hz (e.g., 10 Hz), 15-25 Hz (e.g., 20 Hz), or 35-45 Hz (e.g., 40 Hz). It has been observed by the inventors that a current having such a frequency is capable of increasing blood flow in the subject, e.g., in the limb in which the implant is implanted. Therefore the treatment current is also referred to herein as a bloodflow-increasing current.

Typically, the implant is implanted within a leg of the subject. Further typically, the implant is typically implanted within 10 mm (e.g., within 5 mm, such as within 2 mm) of a tibial nerve of the subject, such that, when activated, the implant applies the treatment current to the tibial nerve.

For some applications, percutaneous electrodes are temporarily introduced into the subject in order to identify an implantation site for implant 22 (e.g., prior to, or as part of, step 66). For some such applications, this is performed using, mutatis mutandis, techniques described in PCT application publication WO 2014/087337 to Gross et al (e.g., with reference to FIGS. 4A-H thereof), which is incorporated herein by reference in its entirety. For some such applications, this is performed using, mutatis mutandis, techniques described in U.S. patent application Ser. No. 14/601,604 to Oron et al., which is incorporated herein by reference in its entirety.

For some applications, the implant may be repositioned or calibrated in response to changes in the subject caused by the implant (box 70). For example, at least in part responsively to a blood-flow change, implant 22 may be repositioned (step 72) or calibrated (step 74). Alternatively (e.g., for a subject that suffers from polyneuropathy in addition to PAOD) implant 22 may be configured to relieve pain (e.g., as described hereinbelow) as well as to increase blood flow, and at least in part responsively to a level of pain relief and/or of paresthesia, the implant may be repositioned (step 76) or calibrated (step 78). For some applications, both (i) a blood-flow change and (ii) a level of pain relief and/or paresthesia are identified, and the implant is repositioned and/or calibrated at least in part responsively to both (i) the blood-flow change and (ii) the level of pain relief and/or paresthesia. Blood-flow change may be detected using the same, or a different, technique to the technique used to identify the subject as having PAOD. For example, blood-flow change may be detected using one or more of the factors described hereinbelow with reference to FIGS. 4 & 5, mutatis mutandis.

For some applications, implant 22 is configured to relieve pain by inducing paresthesia. For some applications, implant 22 is configured to relieve pain via high-frequency nerve blocking.

Steps 72, 74, 76 and 78 are contained within box 70, with no arrows therebetween, so as to illustrate that these steps may be performed in any order, and may be repeated, as necessary. For some applications, Calibration of implant 22 typically comprises changing an characteristic of the treatment current, such as amplitude, frequency and/or pulse width. Calibration is typically performed wirelessly. Repositioning of implant 22 is typically performed before the implant has been fully deployed (e.g., fully released from introducer 40). For some applications, implant 22 is repositioned using, mutatis mutandis, techniques described in PCT application publication WO 2014/087337 to Gross et al. (e.g., with reference to FIGS. 1A-3 thereof), which is incorporated herein by reference in its entirety.

For some applications, the implant is implanted in a subject that does not suffer from peripheral polyneuropathy (e.g., does not suffer from pain caused by polyneuropathy). That is, for some applications, identifying the subject comprises also identifying that the subject does not suffer from peripheral polyneuropathy (step 64).

Figure 3:
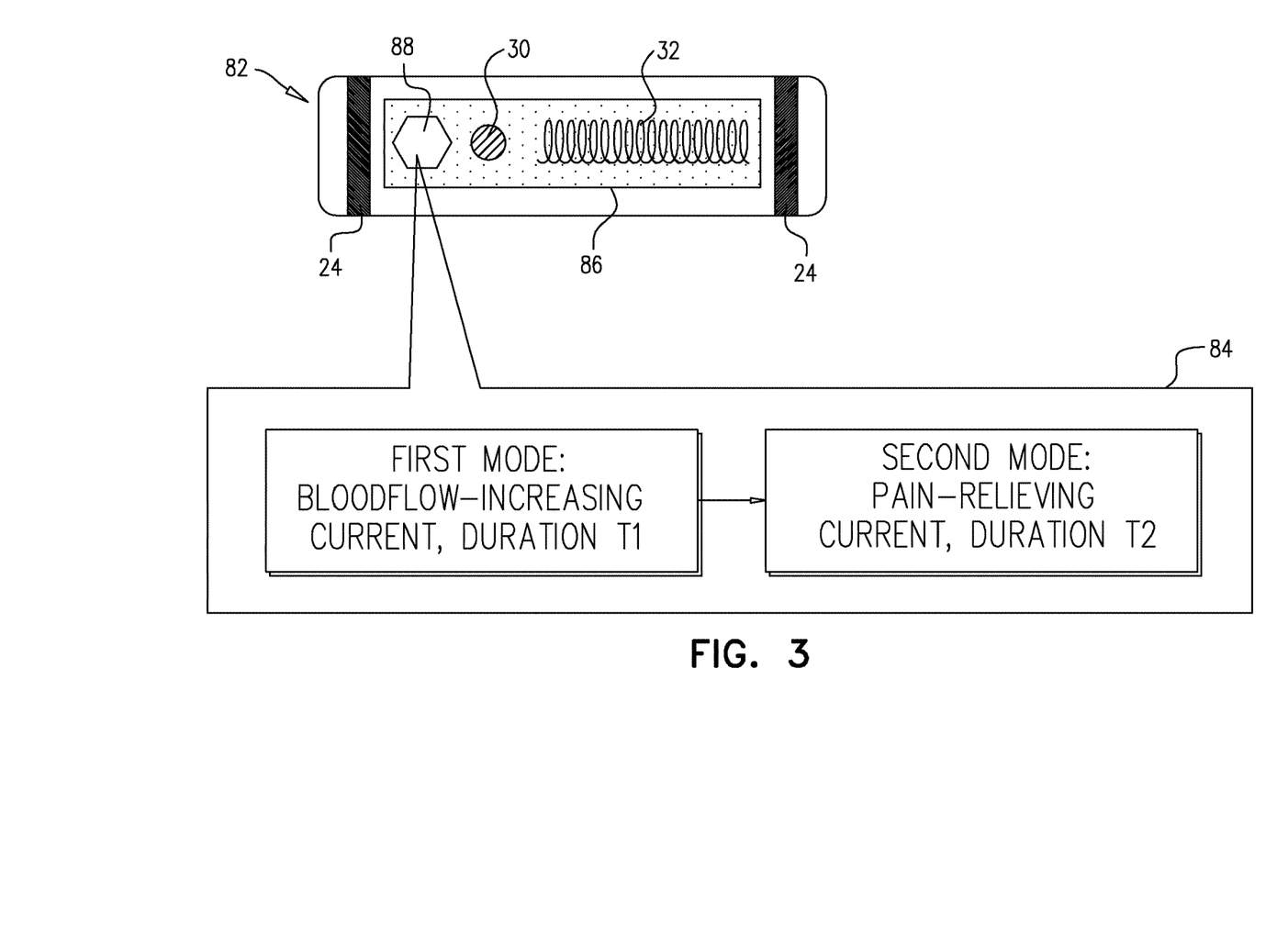
FIG. 3 is a schematic illustration of an implant, in accordance with some applications of the invention.

Reference is made to FIG. 3, which is a schematic illustration of an implant 82, in accordance with some applications of the invention. Implant 82 is identical to implant 22, except where noted, and may be used with techniques described herein as described for implant 22, mutatis mutandis. Implant 82 is typically used in subjects that suffer from both PAOD and polyneuropathy.

Circuitry 86 (e.g., a control unit 88 thereof) of implant 82 is configured to alternate the implant between a first mode in which the implant applies a first current, and a second mode in which the implant applies a second current that differs in at least one characteristic (such as, but not limited to, frequency, amplitude, or pulse width) from the first current. Box 84 schematically illustrates this alternating between the first and second modes. The first current is the bloodflow-increasing current described hereinabove, and the second current is configured to induce pain relief. For some applications, the implant is calibrated to adjust one or both of the currents for the particular subject. For some applications, implant 82 remains in the first mode for a duration of 1-30 min (e.g., 2-20 min, such as 5-15 min). For some applications, implant 82 remains in the second mode for a duration of 1-30 min (e.g., 2-20 min, such as 5-15 min). The duration of the first mode may be the same as, or different from, the duration of the second mode.

As described hereinabove, the bloodflow-increasing first current has a frequency of 1-100 Hz. For applications in which pain relief is provided by inducing paresthesia, the second current may also have a frequency of 1-100 Hz. For applications in which pain relief is provided by high frequency nerve blocking, the second current typically has a frequency of 1-10 kHz.

Figure 4:
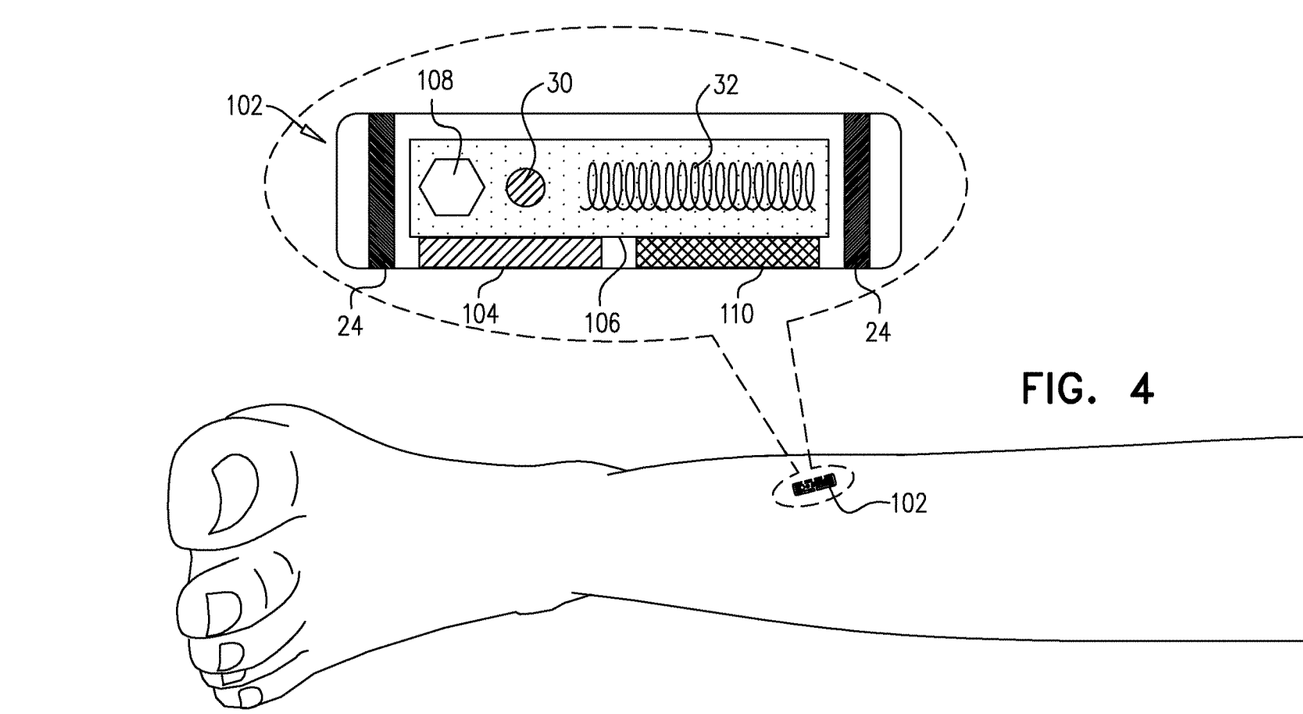
FIG. 4 is a schematic illustration of an implant 102, in accordance with some applications of the invention.

Reference is made to FIG. 4, which is a schematic illustration of an implant 102, in accordance with some applications of the invention. Implant 102 is identical to implant 22, except where noted, and may be used with techniques described herein as described for implant 22, mutatis mutandis. Implant 102 comprises at least one sensor, configured to detect a respective factor indicative of local blood supply (e.g., indicative of blood perfusion to the tissue in which the implant is disposed, or indicative of blood flow through a nearby artery). For illustrative purposes, implant 102 is shown as having a first sensor 104 and a second sensor 110. Circuitry 106 (e.g., a control unit 108 thereof) of implant 102 is configured to drive electrodes 24 to apply the bloodflow-increasing current to the tissue at least in part responsively to the detected factor, typically so as to provide feedback-based treatment as required.

For some applications, one of sensors 104 and 110 is a temperature sensor, configured to detect temperature of the tissue in which the implant is implanted. For such applications, circuitry 106 (e.g., a control unit 108 thereof) of implant 102 is configured to drive electrodes 24 to apply the bloodflow-increasing current to the tissue at least in part responsively to the detected temperature, typically if the detected temperature drops below a threshold temperature, the drop in temperature being indicative of reduced blood flow in the limb.

For some applications, one of sensors 104 and 110 is configured to detect an oxygen saturation in the tissue in which the implant is disposed. For example, the sensor may be an oximeter. For such applications, circuitry 106 (e.g., control unit 108) is configured to drive electrodes 24 to apply the blood-flow increasing current at least in part responsively to the detected oxygen saturation. For example, at least in part responsively to the detected oxygen saturation being indicative of reduced blood flow in the limb (e.g., being lower than a threshold saturation), circuitry 106 (e.g., control unit 108) drives electrodes 24 to apply the bloodflow-increasing current.

For some applications, one of sensors 104 and 110 is a pressure sensor, configured to detect a blood pressure factor. For such applications, circuitry 106 (e.g., control unit 108) is configured to drive electrodes 24 to apply the blood-flow increasing current at least in part responsively to the detected blood pressure factor. For some such applications, the detected blood pressure factor comprises pulse pressure, and circuitry 106 (e.g., control unit 108) is configured to drive electrodes 24 to apply the bloodflow-increasing current at least in part responsively to the detected pulse pressure. For example, at least in part responsively to the detected blood pressure factor (e.g., pulse pressure) being indicative of reduced blood flow in the limb, circuitry 106 (e.g., control unit 108) drives electrodes 24 to apply the bloodflow-increasing current.

For some applications, one of sensors 104 and 110 is an accelerometer, configured to detect movement of the implant caused by expansion of an artery of the limb in which the implant is disposed. For such applications, circuitry 106 (e.g., control unit 108) is configured to drive electrodes 24 to apply the blood-flow increasing current at least in part responsively to the detected movement. For example, at least in part responsively to the detected movement being indicative of reduced blood flow in the limb, circuitry 106 (e.g., control unit 108) drives electrodes 24 to apply the bloodflow-increasing current. For such applications, circuitry 106 (e.g., control unit 108 thereof) is configured to distinguish movement of the implant caused by expansion of an artery, from movement of the implant caused by movement of the limb.

It is to be noted that implant 102 may comprise one or more of the above-described sensors, and circuitry 106 (e.g., control unit 108) may be configured to drive electrodes 24 to apply the blood-flow increasing current at least in part responsively to any combination of the detected factors.

Figure 5:
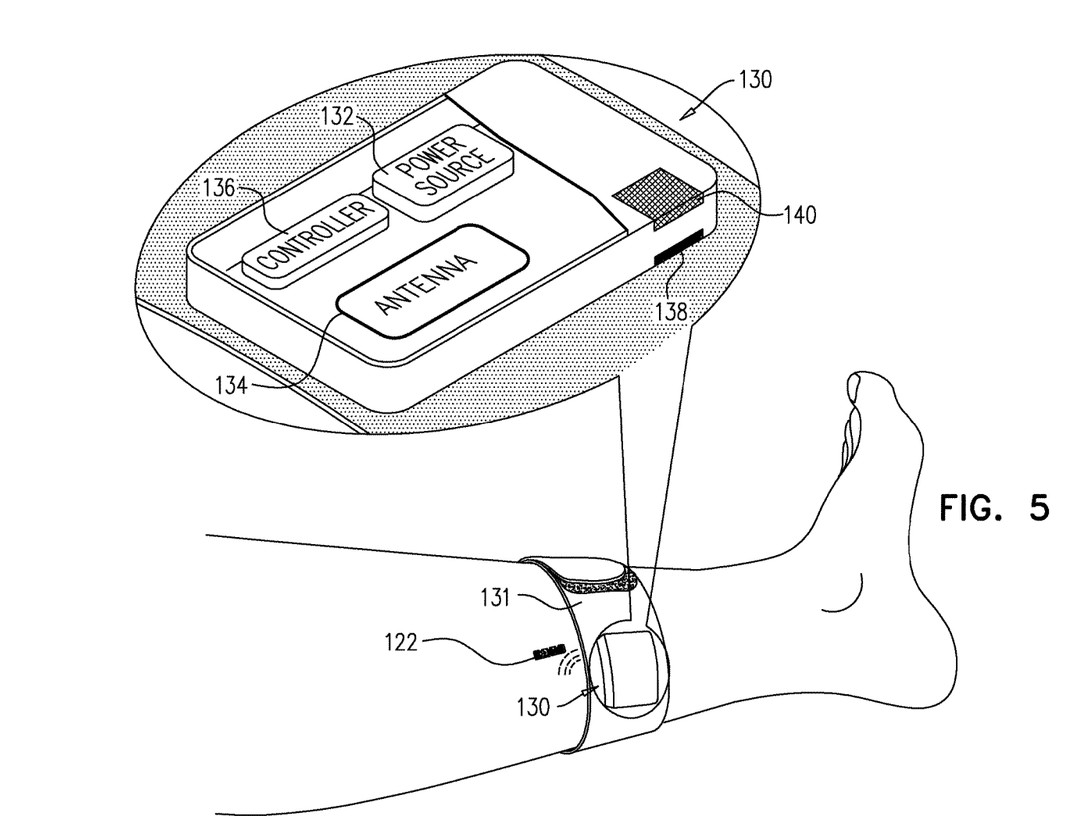
FIG. 5 is a schematic illustration of a system comprising an implant and an extracorporeal device, in accordance with some applications of the invention.

Reference is made to FIG. 5, which is a schematic illustration of a system 120 comprising an implant 122 and an extracorporeal device 130, in accordance with some applications of the invention. Implant 122 is identical to implant 102, except where noted, and may be used with techniques described herein as described for implant 102, mutatis mutandis. Extracorporeal device 130 is configured to be attached to the limb in which implant 122 is disposed, such as by comprising a strap 131 that is extendable around the limb.

Extracorporeal device 130 comprises a power source (e.g., a battery) 132, an antenna 134, and a controller 136 that uses power from source 132 to drive antenna 134 to transmit wireless power, which is received by antenna 32 of implant 122, as described hereinabove, mutatis mutandis. For some applications, device 130 is configured to wirelessly drive (e.g., via circuitry of implant 122) one or more of the sensors (e.g., sensor 104 or sensor 110) of implant 122, and to receive from the implant information regarding the detected factor(s). At least in part responsively to this received information, controller 136 drives antenna 134 to wirelessly drive circuitry 106 (e.g., control unit 108 thereof) to drive electrodes 24 to apply the bloodflow-increasing current. That is, system 120 has similar overall functionality to implant 102, but with at least part of the information processing performed by extracorporeal device 130 rather than by the implant, thereby facilitating miniaturization of implant 122.

It is to be noted that antenna 134 may extend around part, most, or all of strap 131, so as to facilitate communication with implant 122.

For some applications, extracorporeal device 130 comprises at least one extracorporeal sensor, such as an extracorporeal sensor 138 and/or an extracorporeal sensor 140. Sensor 138 is an example of a sensor that is positioned to face the skin of the subject (e.g., to be placed in contact with the skin) when device 130 is attached to the limb, and sensor 140 is an example of a sensor that is typically positioned to face away from the skin of the subject when device 130 is attached to the limb. Typically, sensor 138 is configured to detect a factor indicative of local blood supply, and sensor 140 is configured to detect a factor of the environment. For example, for some applications, sensor 138 is an extracorporeal temperature sensor configured to detect a temperature of the limb, and sensor 140 is an extracorporeal temperature sensor configured to detect an ambient temperature. For such applications, controller 136 is configured to receive information regarding the temperature detected by at least one of the extracorporeal temperature sensors, and device 130 is configured to wirelessly drive circuitry 106 (e.g., control unit 108) of implant 122 to drive electrodes 24 to apply the bloodflow-increasing current to the tissue, at least in part responsively to the temperature detected by the at least one extracorporeal temperature sensor.

Alternatively or additionally, one or more of the extracorporeal sensors may be an oximeter, a pressure sensor, and/or an accelerometer, e.g., as described hereinabove for sensors 104 and 110, mutatis mutandis.

For some applications, the bloodflow-increasing current is driven in response to both (i) information received from the intracorporeal sensors of implant 122, and (ii) information received from the extracorporeal sensors of device 130.

For some applications, extracorporeal device 130 (e.g., controller 136 thereof) is configured to drive implant 122 to alternate between the first and second modes described with reference to FIG. 3, mutatis mutandis.

Reference is again made to FIGS. 1-5. Antennas are shown schematically, and unless described specifically, the configuration (e.g., the shape) of each antenna is not necessarily as shown. Furthermore, whereas each implant and extracorporeal device is shown as comprising a single antenna, that antenna may represent one or more antennas. For example, for some applications that single antenna performs both power transfer and information transfer, whereas for some applications, these functions are performed by distinct antennas.

Reference is again made to FIGS. 1-5. For some applications, the apparatus described herein is used with a limb that does not exhibit PAOD. For example, the apparatus may be used in a currently-unaffected limb of a subject that suffers from PAOD, or in a subject that is identified as being at increased risk of developing PAOD in the future. It is hypothesized that, for some applications, such uses of the apparatus described herein may delay or prevent the development of PAOD (or symptoms thereof) in the treated limb.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating a subject who suffers from both peripheral artery occlusive disease and polyneuropathy, the apparatus comprising:
    an implant, comprising:
        an injectable housing,
        an electrode disposed on an outer surface of the housing, and
        circuitry, configured:
            (i) with a first mode in which the circuitry drives the electrode to apply a first electrical current having a frequency of 1-100 Hz,
            (ii) with a second mode in which the implant applies a second electrical current having a frequency of 1-10 kHz, and
            (iii) to alternate the implant between the first mode and the second mode; and
    an introducer:
        comprising a tube defining a lumen, the tube being percutaneously-advanceable into tissue of the subject, and the lumen dimensioned to at least temporarily house the implant, and
        configured to deploy the implant from a distal end of the lumen by moving the implant and the distal end of the lumen relative to each other.

2. The apparatus according to claim 1, wherein the implant further comprises a temperature sensor, configured to detect a temperature of the tissue, and wherein the circuitry is configured to drive the electrode to apply the first electrical current in response to the detected temperature being below a threshold temperature.

3. The apparatus according to claim 1, wherein the implant further comprises a pressure sensor, configured to detect a pressure within the tissue, and the circuitry is configured to drive the electrode to apply the first electrical current at least in part responsively to the detected pressure.

4. The apparatus according to claim 3, wherein the pressure comprises a pulse pressure, and the circuitry is configured to drive the electrode to apply the first electrical current at least in part responsively to the detected pulse pressure.

5. The apparatus according to claim 1, wherein the implant further comprises an oximeter, configured to detect an oxygen saturation within the tissue, and the circuitry is configured to drive the electrode to apply the first electrical current at least in part responsively to the detected oxygen saturation.

6. The apparatus according to claim 1, wherein the circuitry is configured to remain in the first mode for a first-mode duration of 1-30 minutes.

7. The apparatus according to claim 6, wherein the circuitry is configured to remain in the first mode for a first-mode duration of 2-20 minutes.

8. The apparatus according to claim 7, wherein the circuitry is configured to remain in the first mode for a first-mode duration of 5-15 minutes.

9. The apparatus according to claim 1, wherein the circuitry is configured to remain in the second mode for a second-mode duration of 1-30 minutes.

10. The apparatus according to claim 9, wherein the circuitry is configured to remain in the second mode for a second-mode duration of 2-20 minutes.

11. The apparatus according to claim 10, wherein the circuitry is configured to remain in the second mode for a second-mode duration of 5-15 minutes.

12. The apparatus according to claim 1, wherein the circuitry is configured to remain in the first mode for a first-mode duration, and to remain in the second mode for a second-mode duration that is the same as the first-mode duration.

13. The apparatus according to claim 1, wherein the circuitry is configured to remain in the first mode for a first-mode duration, and to remain in the second mode for a second-mode duration that is different from the first-mode duration.

* * * * *